United States Patent
Nishida et al.

(10) Patent No.: US 10,258,247 B2
(45) Date of Patent: Apr. 16, 2019

(54) METHOD AND APPARATUS FOR ANALYZING NUCLEAR MEDICINE IMAGE OF MYOCARDIA

(71) Applicant: Nihon Medi-Physics Co., Ltd., Tokyo (JP)

(72) Inventors: Kazumasa Nishida, Tokyo (JP); Kazuo Hamada, Tokyo (JP); Kazunori Kobayashi, Tokyo (JP)

(73) Assignee: Nihon Medi-Physics Co. Ltd., Tokyo (JP)

( * ) Notice: Subject to any disclaimer, the term of this patent is extended or adjusted under 35 U.S.C. 154(b) by 0 days.

(21) Appl. No.: 15/451,686

(22) Filed: Mar. 7, 2017

(65) Prior Publication Data

US 2017/0354333 A1    Dec. 14, 2017

(30) Foreign Application Priority Data

Jun. 10, 2016   (JP) ................................ 2016-115778

(51) Int. Cl.
| | |
|---|---|
| A61B 5/026 | (2006.01) |
| A61B 6/00 | (2006.01) |
| A61B 6/03 | (2006.01) |
| A61B 5/00 | (2006.01) |
| G06T 7/00 | (2017.01) |

(52) U.S. Cl.
CPC .......... *A61B 5/0263* (2013.01); *A61B 5/7203* (2013.01); *A61B 5/7278* (2013.01); *A61B 6/037* (2013.01); *A61B 6/507* (2013.01); *A61B 6/5205* (2013.01); *A61B 6/5217* (2013.01);
(Continued)

(58) Field of Classification Search
None
See application file for complete search history.

(56) References Cited

U.S. PATENT DOCUMENTS

| | | | |
|---|---|---|---|
| 5,970,182 A * | 10/1999 | Goris | G06T 3/0081 |
| | | | 382/128 |
| 7,848,557 B2 * | 12/2010 | Kadrmas | G01T 1/1611 |
| | | | 378/4 |

(Continued)

FOREIGN PATENT DOCUMENTS

WO    WO-2016/088492 A1    6/2016

OTHER PUBLICATIONS

Jekic et al., "Cardiac function and myocardial perfusion immediately following maximal treadmill exercise inside the MRI room," Journal of Cardiovascular Magnetic Resonance, 2008, vol. 10, No. 3.*

(Continued)

*Primary Examiner* — Soo Shin
(74) *Attorney, Agent, or Firm* — Harrington & Smith

(57) ABSTRACT

Provided is a highly reliable technique for the evaluation of ischemic conditions. A preferred embodiment is a nuclear medicine measurement protocol in which the administration of a radiopharmaceutical agent and radiation measurement are performed twice at rest and under stress. In the nuclear medicine measurement protocol, radiation collection is performed without radiopharmaceutical agent administration before the second radiopharmaceutical agent administration, and the result is used to correct the nuclear medicine measurement result after the second radiopharmaceutical agent administration.

21 Claims, 7 Drawing Sheets

(52) U.S. Cl.
CPC .. *G06T 7/0016* (2013.01); *G06T 2207/10108* (2013.01); *G06T 2207/30104* (2013.01)

(56) References Cited

U.S. PATENT DOCUMENTS

| | | | | |
|---|---|---|---|---|
| 8,155,408 | B2* | 4/2012 | Ranga | G06K 9/6807 382/128 |
| 2011/0293519 | A1* | 12/2011 | Mishani | A61K 51/0406 424/1.85 |
| 2012/0041318 | A1* | 2/2012 | Taylor | A61B 5/02007 600/504 |
| 2013/0064769 | A1* | 3/2013 | Cesati | C07D 237/16 424/1.89 |
| 2014/0121511 | A1 | 5/2014 | Kadrmas et al. | |
| 2014/0328756 | A1* | 11/2014 | Radeke | C07D 209/14 424/1.89 |

OTHER PUBLICATIONS

Goetze et al., "Attenuation Correction in Myocrdial Perfusion SPECT/CT: Effects of Misregistration and Value of Reregistration," The Journal of Nuclear Medicine, vol. 48, No. 7, Jul. 2007.*

Yamauchi et al., "Quantitative assessment of rest and acetazolamide CBF using quantitative SPECT reconstruction and sequential adminimistration of 123I-iodamphetamine: comparison among data acquired at three institutions," Annu Nucl Med (2014) 28:836-850.*

M. F. Di Carli et al. "*Clinical Myocardial Perfusion PET/CT*" The Journal of Nuclear Medicine vol. 48, No. 5, May 1, 2007. pp. 783-793, XP055190987.

Stephan Nekolla et al. "*The Effect of Different Normalizations for the Quantification of Myocardial F-18 FDG Uptake*" J Nucl Med, vol. 56, May 1, 2015 XP055397666.

Sugawara, Yoshifurni, et al., "Reevaluation of the Standardized Uptake Value for FDG: Variations with Body Weight and Methods for Correction" Radiology 1999, vol. 213, No. 2, 5 pgs.

* cited by examiner

METHOD AND APPARATUS FOR ANALYZING NUCLEAR MEDICINE IMAGE OF MYOCARDIA

BACKGROUND OF THE INVENTION

1. Field of the Invention

The present application relates to a method of analyzing myocardial nuclear medicine image data and an apparatus for analyzing myocardial nuclear medicine image data.

2. Description of the Related Art

Nuclear medicine technology is used to yield various types of physiological and biochemical information about the heart in many cases. Specifically, a single-photon emission computed tomography (SPECT) examination has excellent characteristics including an easy load examination, a high examination success rate and low invasiveness.

An application field of nuclear medicine imaging examination on the heart is the detection of ischemia. The detection of ischemia is performed by comparing a nuclear medicine image recorded at rest with a nuclear medicine image recorded under stress.

The primary image obtained from nuclear medicine measurement is prepared by the imaging of radiation count values or tissue radioactivity concentrations. Pixels corresponding to the position at which a tracer is highly accumulated have a large pixel value and are displayed brightly. However, the radiation count value or the tissue radioactivity concentration is affected by various factors, and thus even when particular pixels have a pixel value different from those of the other positions, whether the corresponding tissue is abnormal is not necessarily evident. To address this uncertainness, attempts have been made to normalize pixel values in accordance with a certain rule so as to enable quantitative evaluation of the pixel values. As such a quantitative value, a standardized uptake value (SUV) is typically used. The SUV is determined in accordance with the following equation:

$$SUV = \text{Tissue radioactivity concentration}/\{\text{Administered radiation dose/Body mass of subject}\}.$$

In other words, the SUV is calculated by normalization of a tissue radioactivity concentration by the administered radiation dose per body mass. In place of a simple body mass, a lean body mass is used in some cases (Non-Patent Document 1).

[Non-Patent Document 1] Yoshifumi Sugawara, Kenneth R. Zasadny et al., "Reevaluation of the Standardized Uptake Value for FDG: Variations with Body Weight and Methods for Correction", November 1999 Radiology, 213, 521-525.

SUMMARY OF THE INVENTION

The existing SUV is determined on the assumption that a tracer is evenly distributed in the whole body or muscle. In the case of the nuclear medicine examination of the heart, a tracer is, however, accumulated mainly in myocardia, and thus the assumption of the existing SUV may be inappropriate. On this account, there is a demand for a novel technique for quantitatively evaluating tracer accumulation.

Existing ischemia detection methods are reported to have a possibility of underestimating ischemic conditions of patients with a diffusely lowered myocardial blood flow, including patients with multivessel ischemic cardiomyopathy. There is thus a demand for a highly reliability technique for evaluating ischemic conditions.

The invention disclosed in the present application is intended to solve at least one of the above-described problems.

An embodiment of the invention described in the present application is intended to normalize image data obtained from myocardial nuclear medicine measurement, using a value relating to the size of the heart.

In a preferred embodiment, the pixel value of each pixel of the myocardial nuclear medicine image data is converted into an SUV represented by the following equation:

$$SUV = \text{Tissue radioactivity concentration}/(\text{Administered radiation dose/Value relating to size of heart}).$$

The invention uses a value relating to the size of the heart in which a tracer is accumulated, as a normalization standard to normalize myocardial nuclear medicine image data. The normalization standard thus reflects actual conditions of a cardiac function diagnostic agent more correctly than in the related art. This improves the validity of a normalized value as compared with the related art and enables more appropriate image evaluation than ever.

In the invention, the "value relating to the size of the heart" may be a heart weight, for example. The heart weight may be a myocardial weight, for example. The myocardial weight may be a value obtained by multiplying a myocardial volume by a density factor, for example.

In the invention, the "tissue radioactivity concentration" may be a value obtained by multiplying a pixel value of the myocardial nuclear medicine image data by a becquerel calibration factor (BCF). The BCF is a factor for converting a radiation count value into a radioactivity concentration (for example, Bq/ml). The BCF can be determined by a known method. For example, a nuclear medicine image of a vial (or a syringe) containing a radiopharmaceutical agent having a known total radioactivity can be taken, and the BCF can be calculated in accordance with the following equation:

$$BCF = \text{Decay-corrected total radioactivity (Bq)}/(\text{Total count of all slices/Collection time (seconds)}).$$

To determine the BCF from the data obtained using a cylindrical phantom, the following equations may be used:

$$\text{Volume factor} = \text{Average count value per slice}/(\text{Volume of single pixel} \times \text{Collection time (seconds)})$$

$$BCF = \text{Decay-corrected total radioactivity (Bq)}/(\text{Phantom volume} \times \text{Volume factor}).$$

In some embodiments, the BCF may be subjected to collection time correction. The collection time correction may be performed by multiplying {Volume of single pixel $[cm^3]$/Collection time [sec]} by BCF, for example.

In some myocardial nuclear medicine image data, each pixel value itself may represent a radioactivity concentration.

Needless to say, no conversion using BCF is needed in such a case.

An embodiment of the invention includes the following method, which is the method for processing myocardial nuclear medicine image data.

This method includes operating the apparatus as first means for storing a heart parameter serving as a value relating to a size of a heart and as second means for storing an administered radiation dose.

This method also includes converting pixel values of at least part of pixels of the image data using the values stored in the first means and the second means into SUVs in accordance with the following equation, and storing the SUVs:

$$SUV = \text{Tissue radioactivity concentration}/(\text{Administered radiation dose}/\text{Value based on heart parameter}).$$

In some embodiments, the heart parameter is a myocardial weight, and the value based on the heart parameter is also a myocardial weight.

In some embodiments, the heart parameter is a myocardial volume, and the value based on the heart parameter is a myocardial weight calculated by multiplying the myocardial volume by a conversion factor.

An embodiment of the invention includes a computer program including a program instruction configured to cause an apparatus to perform the above-described method when the computer program is executed by processing means in the apparatus.

Another embodiment of the invention includes an apparatus including processing means and memory means. The memory means stores a program instruction, and the program instruction is configured to perform the above-described method when the program instruction is executed by the processing means.

Another embodiment of the invention described in the present application is a nuclear medicine measurement protocol in which the administration of a radiopharmaceutical agent and radiation measurement are performed twice at rest and under stress. In the nuclear medicine measurement protocol, radiation collection is performed without radiopharmaceutical agent administration before the second radiopharmaceutical agent administration, and the result is used to correct the subsequent nuclear medicine measurement results after the second radiopharmaceutical agent administration.

In the present description, the radiation collection performed before the second radiopharmaceutical agent administration is referred to as prescan. The prescan is performed immediately before later measurement between the measurement under stress and the measurement at rest and is performed immediately before the radiopharmaceutical agent administration for the later measurement.

When the time interval between the measurement at rest and the measurement under stress is insufficient, the nuclear medicine data obtained through the later nuclear medicine measurement is affected by the radiopharmaceutical agent administration for the earlier nuclear medicine measurement. With the above-described invention, such an effect can be corrected by data collection results of the prescan. The pieces of nuclear medicine data are thus compared between at rest and under stress more accurately. In the existing examination, the second nuclear medicine measurement can be performed only after no effect of the first radiopharmaceutical agent administration is observed. The above-described invention can correct such an effect and thus shorten the time interval between the measurement at rest and the measurement under stress. In the existing examination, the measurement at rest and the measurement under stress need to be performed on different days, for example. The above-described invention allows the two measurements to be performed successfully on the same day.

An embodiment of the invention includes the following method, which is the method of processing myocardial nuclear medicine image data for determining the increase rate of blood flow under stress relative to blood flow at rest. This method includes:

storing at least part of first myocardial nuclear medicine image data collected earlier between myocardial nuclear medicine image data collected at rest and myocardial nuclear medicine image data collected under stress;

storing at least part of second myocardial nuclear medicine image data collected between the nuclear medicine image data collection at rest and the nuclear medicine image data collection under stress, the second myocardial nuclear medicine image data being collected before administration of a radiopharmaceutical agent for later data collection between the myocardial nuclear medicine image data at rest and the myocardial nuclear medicine image data under stress;

storing at least part of third myocardial nuclear medicine image data collected later between the myocardial nuclear medicine image data collected at rest and the myocardial nuclear medicine image data collected under stress;

correcting at least part of the third myocardial nuclear medicine image data using at least part of the second myocardial nuclear medicine image data to eliminate an effect of remaining radioactivity from the first myocardial nuclear medicine image data remaining in the third myocardial nuclear medicine image data; and determining the blood flow increase rate using at least part of the first myocardial nuclear medicine image data and at least part of the third myocardial nuclear medicine image data after the correction.

In some embodiments, the above-described method may further include:

operating the apparatus as first means for storing a heart parameter serving as a value relating to a size of a heart and as second means for storing an administered radiation dose;

converting pixel values of at least part of pixels of the image data using the values stored in the first means and the second means into SUVs in accordance with the following equation, and storing the SUVs:

$$SUV = \text{Tissue radioactivity concentration}/(\text{Administered radiation dose}/\text{Value based on heart parameter}); \text{ and}$$

determining the blood flow increase rate using at least part of the SUVs.

In some embodiments, the heart parameter may be a myocardial weight, and the value based on the heart parameter may also be a myocardial weight. In some embodiments, the heart parameter may be a myocardial volume, and the value based on the heart parameter may be a myocardial weight calculated by multiplying the myocardial volume by a conversion factor.

In some embodiments, the above-described method may further include converting the first to third myocardial nuclear medicine image data into two-dimensional array data or polar maps, and calculating the myocardial blood flow increase rate using the data after the conversion.

An embodiment of the invention includes a computer program including a program instruction configured to cause an apparatus to perform the above-described method when the computer program is executed by processing means in the apparatus.

Another embodiment of the invention includes an apparatus including processing means and memory means. The memory means stores a program instruction, and the program instruction is configured to perform the above-described method when the program instruction is executed by the processing means.

Some embodiments of the invention of the present application thought to be preferred now are specified by the appended claims. However, the configurations specified by these claims do not necessarily completely encompass all the novel technical spirit disclosed in the description and the drawings of the present application. It should be noted that the applicant claims a right to the patent of all the novel technical spirit disclosed in the description and the drawings of the present application regardless of whether the technique is described in the present claims.

DETAILED DESCRIPTION OF THE PREFERRED EMBODIMENTS

Preferred embodiments of the technical spirit disclosed in the present application will now be described with reference to the attached drawings.

Figure 1:
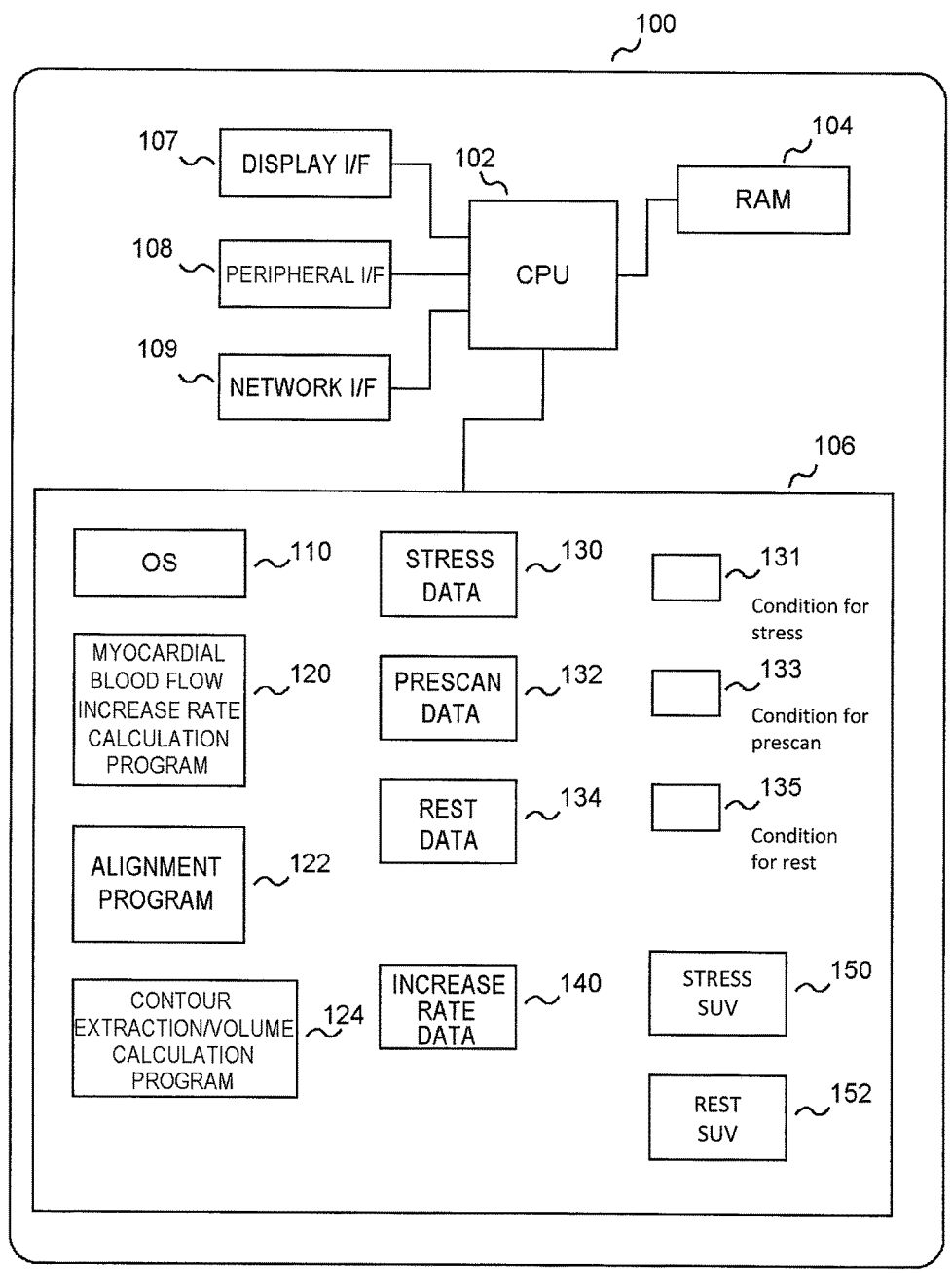
FIG. 1 is a diagram for explaining a hardware configuration of a system capable of performing the present invention.

FIG. 1 is a diagram for explaining a hardware configuration of a system 100 capable of performing the present invention. As illustrated in FIG. 1, the hardware configuration of the system 100 is substantially the same as those of conventional computers, and can include a CPU 102, a main memory unit 104, a mass storage unit 106, a display interface 107, a peripheral interface 108, and a network interface 109, for example. Similarly to conventional computers, the main memory unit 104 may be a high-speed random access memory (RAM), and the mass storage unit 106 may be an inexpensive, large-capacity hard disk or SSD. The system 100 may be connected to a display for displaying information via the display interface 107. The system 100 may also be connected to user interfaces, such as a keyboard, a mouse, and a touch panel, via the peripheral interface 108. The network interface 109 can be used to connect the system to other computers and the Internet via a network.

The mass storage unit 106 stores an operating system (OS) 110, a myocardial blood flow increase rate calculation program 120, an alignment program 122, and a contour extraction/volume calculation program 124. The most basic function of the system 100 is provided through execution of the OS 110 by the CPU 102. The myocardial blood flow increase rate calculation program 120 includes program instructions relating to the novel processing disclosed in the present application. Through execution of at least part of these instructions by the CPU 102, the system 100 can perform the novel processing disclosed in the present application.

The alignment program 122 includes instructions for adjusting the positions or the sizes of images to each other between a plurality of pieces of nuclear medicine image data. The existing commercially available positron emission tomography (PET) or SPECT apparatuses typically include such a program, and all or part of the program can be used as the alignment program 122.

The contour extraction/volume calculation program 124 includes instructions for extracting the myocardial contour. Some algorithms and software for myocardial contour extraction are known, and such an algorithm is disclosed by the present applicant in PCT International Publication (WO2013/047496A1), for example. In addition, QGS by Cedras-Sinai Medical Center, 4D-MSPECT by the University of Michigan, and pFAST by Sapporo Medical University are also disclosed as the algorithm or software for myocardial contour extraction. The program instructions included in the contour extraction/volume calculation program 124 may be configured to extract the myocardial contour using such an algorithm or software and to calculate the volume of the extracted myocardium. An embodiment of the invention disclosed in the present application can be operated together with various myocardial contour extraction algorithms, but the algorithm described in WO2013/047496A1 is preferably used to extract the myocardial contour because the algorithm has high extraction accuracy.

The mass storage unit 106 can further store three-dimensional nuclear medicine image data 130, three-dimensional nuclear medicine image data 132, and three-dimensional nuclear medicine image data 134. Such nuclear medicine image data is to be analyzed or operated by the programs 120, 122, and 124. The mass storage unit 106 can also store collection condition files 131, 133, and 135 that store various data collection conditions relating to the nuclear medicine image data. These pieces of data will be specifically described later. FIG. 1 also illustrates data 140, data 150, and data 152, which will be specifically described later.

The system 100 can also include typical components included in a common computer system, such as a power supply and a cooler, in addition to the units illustrated in FIG. 1. Known embodiments of the computer system can include various forms using various techniques such as distribution, redundancy, and virtualization of memory units, use of multiple CPUs, CPU virtualization, use of a processing-specific processor such as a DSP, and a combination of hardware for particular processing performed by a CPU. The invention disclosed in the present application can be installed on any computer system, and the type of computer system does not limit the scope of the invention. The technical spirit disclosed in the present description can be typically embodied as (1) a program including instructions configured to cause an apparatus or a system including processing means to perform various types of processing described in the present description when the program is executed by the processing means; (2) a method of operating an apparatus or a system implemented by the processing means executing the program; or (3) an apparatus or a system including the program and processing means configured to execute the program, for example. As described above, software processing may be partially made into hardware.

It should be noted that the data 130 to the data 135, for example, is not stored in the mass storage unit 106 in many cases while the system 100 is being produced and sold or is being started. Such data may be transferred from an external device to the system 100 via the peripheral interface 108 or the network interface 109, for example. In some embodiments, the data 131, 133, 135, 140, 150, and 152 may be formed through execution of the myocardial blood flow increase rate calculation program 120 by the CPU 102. Depending on an installed alignment program 122 or an installed OS 110, at least one of the data 131, 133, 135, 140, 150, and 152 is not stored in the mass storage unit 106 but is stored only in the main memory unit 104 in some cases. It should be noted that the scope of the invention disclosed in the present application is not limited by whether the data is included.

Next, the three-dimensional nuclear medicine image data 130, 132, and 134 will be described in detail. These pieces of image data are obtained by nuclear medicine measurement performed for determining a myocardial blood flow increase rate. In the present example, the three-dimensional nuclear medicine image data is obtained using SPECT as a nuclear medicine measurement technique. To determine a myocardial blood flow increase rate, the nuclear medicine image data obtained through nuclear medicine measurement under stress is typically compared with the nuclear medicine image data obtained through nuclear medicine measurement at rest. To determine a myocardial blood flow increase rate, at least the two pieces of nuclear medicine image data are required. In the present example, the data 130 is data obtained through the SPECT data collection immediately after stress application, and the data 134 is data obtained through the SPECT data collection at rest. Hereinafter, the data 130 and the data 134 are also referred to as stress data and rest data, respectively.

In the examples specifically described below, the image data 130, 132, and 134 is image data in which each pixel value corresponds to a radiation count value. In some embodiments, the image data 130, 132, and 134 may be image data in which each pixel value represents a tissue radioactivity concentration.

The protocol of collecting nuclear medicine data to be analyzed in the present application is characterized by collecting radiation emitted from the body of a subject using a nuclear medicine apparatus without administration of a radiopharmaceutical agent between the measurement under stress and the measurement at rest. This radiation collection is referred to as prescan. The prescan is performed immediately before later measurement between the measurement under stress and the measurement at rest, and is performed immediately before a process of data collection in the later measurement. For example, as described later with reference to FIG. 2, the prescan is performed immediately before the application of stress when the later measurement is the measurement of stress data, and the prescan is performed immediately before the administration of a radiopharmaceutical agent when the later measurement is the measurement of rest data. In the present example, the nuclear medicine image data obtained through the prescan is indicated by sign 132. The data to be analyzed in the present application accordingly includes at least three types of data: the stress data 130, the prescan data 132, and the rest data 134.

Figure 2:
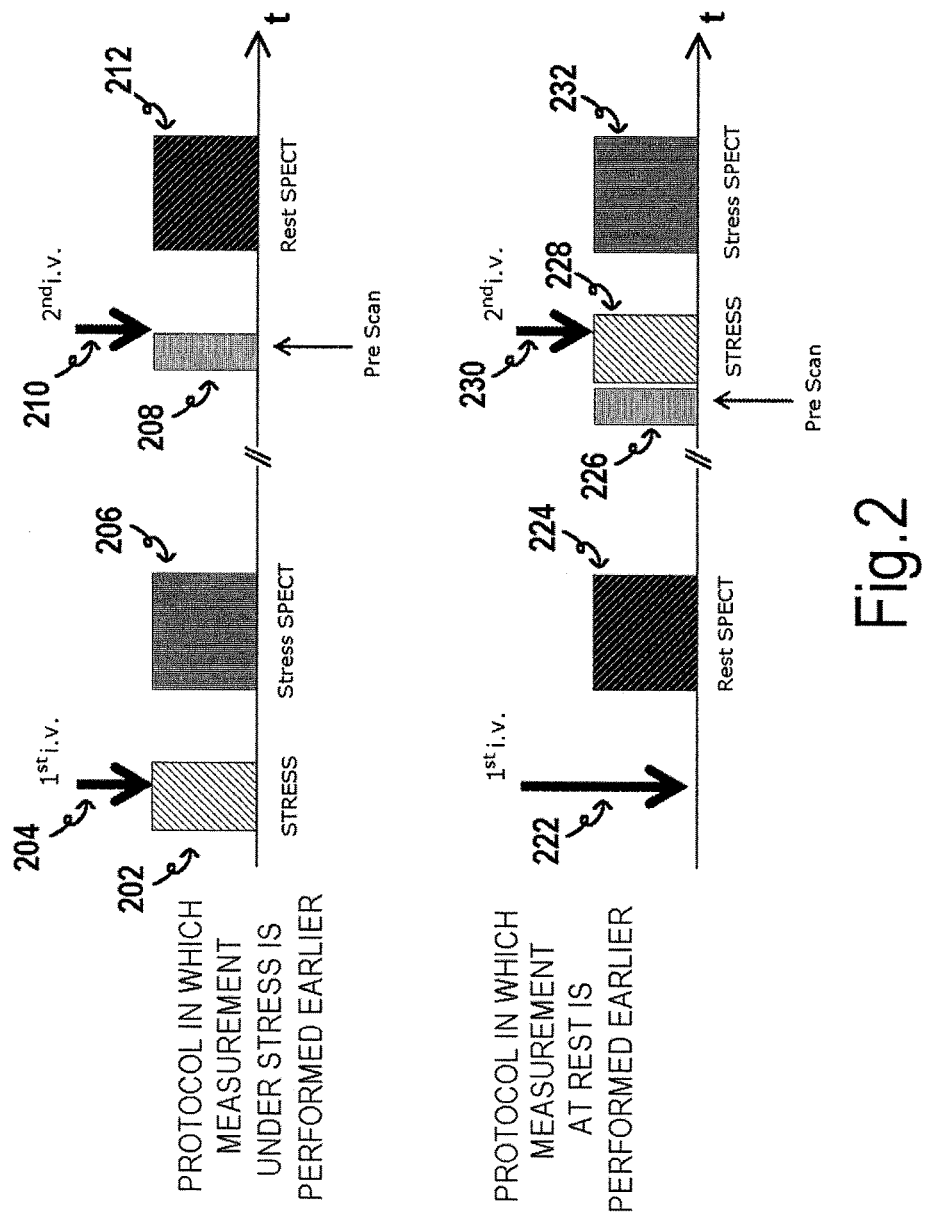
FIG. 2 is a chart for explaining nuclear medicine measurement protocols for obtaining data to be analyzed in the present application.

With reference to FIG. 2, the nuclear medicine measurement protocol for obtaining data to be analyzed in the present application will be described in further detail. FIG. 2 schematically illustrates events performed in protocols on the time axis. As described above, to determine a myocardial blood flow increase rate, nuclear medicine measurement is required to be performed under stress and at rest. In a protocol, the measurement under stress is performed earlier. In another protocol, the measurement at rest is performed earlier.

When the measurement under stress is performed earlier, stress is first applied to a subject (202). The stress may be exercise stress using an ergometer or a treadmill load or drug stress with adenosine or dipyridamole, for example. In the stress application, a radiopharmaceutical agent is administered (intravenous injection) (204). Next, the stress application is stopped, and a nuclear medicine apparatus is used to collect data of radiation emitted from the body of the subject (206). After a certain period of time (several hours), the measurement at rest is performed. Before the measurement at rest, a nuclear medicine apparatus is used to collect data of radiation emitted from the body of the subject without administration of a radiopharmaceutical agent (208). In other words, prescan is performed. Immediately after the completion of the prescan, a radiopharmaceutical agent for measurement at rest is administered (210), and a nuclear medicine apparatus is used to collect data of radiation emitted from the body of the subject (212). The image data obtained through the data collection 206 is the stress data 130, the image data obtained through the data collection 208 is the prescan data 132, and the image data obtained through the data collection 212 is the rest data 134.

When the measurement at rest is performed earlier, a radiopharmaceutical agent for the measurement at rest is first administered to a subject (222), and then a nuclear medicine apparatus is used to collect data of radiation emitted from the body of the subject (224). After a certain period of time (several hours), the measurement under stress is performed. Before the measurement under stress, a nuclear medicine apparatus is used to collect data of radiation emitted from the body of the subject (226) without administration of a radiopharmaceutical agent. In other words, prescan is performed. Immediately after the completion of the prescan, stress application is started (228). In the stress application, a radiopharmaceutical agent for the measurement under stress is administered (230). After the completion of the stress application, a nuclear medicine apparatus is used to collect data of radiation emitted from the body of the subject (232). The image data obtained through the data collection 232 is the stress data 130, the image data obtained through the data collection 226 is the prescan data 132, and the image data obtained through the data collection 224 is the rest data 134.

As described above, in the present example, the nuclear medicine apparatus used for the radiation data collection is an SPECT apparatus, and the radiopharmaceutical agent administered is accordingly a pharmaceutical agent suitable for the radiation data collection by the SPECT apparatus. Examples of known SPECT radiopharmaceutical agents suitable for the nuclear medicine imaging of myocardial blood flow include $^{201}$TlCl (thallium chloride) injection solution, technetium ($^{99m}$Tc) tetrofosmin injection solution, and 15-(4-iodophenyl)-3(R,S)-methylpentadecanoic acid ($^{123}$I) injection solution. The invention disclosed in the present application is applicable to any radiopharmaceutical agent suitable for the nuclear medicine imaging of myocardial blood flow.

Next, the flow of myocardial blood flow increase rate calculation processing 300 of nuclear medicine image data disclosed in the present application will be described with reference to FIG. 3. The processing 300 may be performed by the system 100 in which the myocardial blood flow increase rate calculation program 120 is executed by the CPU 102. In some embodiments, midway through the processing 300, the alignment program 122 or the contour extraction/volume calculation program 124 may be called from the myocardial blood flow increase rate calculation program 120 and executed by the CPU 102 to perform certain processing.

Step 305 indicates the start of processing. In step 310, data to be processed by the myocardial blood flow increase rate calculation program 120 is loaded. In other words, all or part of each of the stress data 130, the prescan data 132, and the rest data 134 is read from the mass storage unit 106 and is stored in the main memory unit 104. The stress data 130, the prescan data 132, and the rest data 134 may be directly imported from an external nuclear medicine apparatus into the main memory unit 104 via the network interface 109.

In step 315, a data collection protocol is identified. In other words, a protocol in which the stress data 130, the prescan data 132, and the rest data 134 have been collected is identified as either the protocol in which the measurement under stress is performed earlier or the protocol in which the measurement at rest is performed earlier. The identification may be performed by comparing time information (for example, data collection start time) contained in the stress data 130 and the rest data 134, for example. For example, when the collection start time of the stress data 130 is earlier than the collection start time of the rest data 134, such a protocol can be identified as the protocol in which the measurement under stress is performed earlier. When the collection start time of the stress data 130 is later than the collection start time of the rest data 134, such a protocol can be identified as the protocol in which the measurement at rest is performed earlier. In some embodiments, an operator can input protocol identification information into the system 100 to allow the system 100 to specify the data collection protocol.

The determination of the data 130 as stress data may be made by identification information contained in the data 130. Similarly, the determination of the data 134 as rest data may be made by identification information contained in the data 134.

In step 320, various collection conditions of the stress data 130, the prescan data 132, and the rest data 134 are retrieved. The various collection conditions include the following information, for example.

A radiation dose measured before administration of a radiopharmaceutical agent to a subject (radiation dose before administration). For example, a value obtained by measuring the radiation dose of a whole administration syringe containing a radiopharmaceutical agent to be administered The measurement date and time of a radiation dose before administration The date and time at the start of data collection The data collection time A radiation dose measured after administration of the radiopharmaceutical agent to the subject (radiation dose after administration). For example, a measurement value of the radiation dose remaining in the syringe after administration The measurement date and time of a radiation dose after administration The half-life of a tracer contained in the radiopharmaceutical agent Becquerel calibration factor (BCF, a factor for converting a radiation count value into a radioactivity concentration (for example, Bq/ml))

In some embodiments, these collection conditions may be included in the stress data 130, the prescan data 132, and the rest data 134. In such a case, the system 100 may read the information from the data 130 to 134 and store the information in the main memory unit 104 or the mass storage unit 106.

In some embodiments, the system 100 may be configured to create and display a user interface (for example, a dialog box) to which an operator inputs these collection conditions. When an operator inputs intended collection conditions, the system 100 may store these collection conditions in the main memory unit 104 or the mass storage unit 106.

In an embodiment in which each pixel value of image data 130 to the data 134 represents a tissue radioactivity concentration, the BCF is not used and thus is not required to be retrieved.

Of the above-described collection conditions, information required may vary with embodiments. Some embodiments of step 345 will be specifically described later, and information required varies with these embodiments. Information required may differ among the stress data 130, the rest data 134, and the prescan data 132. The system 100 may create and display different user interfaces depending on collection condition data to be input, (i.e., depending on whether the data is the stress data 130, the prescan data 132, or the rest data 134), and the respective user interfaces may be configured to be convenient for inputting specific data required for the data.

As described above, the system 100 may be configured to store the retrieved collection condition information in the main memory unit 104 or the mass storage unit 106. In the present example, the collection condition information for the stress data 130 is considered to be stored in a collection condition file 131, the collection condition information for the prescan data 132 is considered to be stored in a collection condition file 133, and the collection condition information for the rest data 134 is considered to be stored in a collection condition file 135, for example.

In step 325, whether data 132 is the prescan data is determined, as needed. In some embodiments, the determination may be made by identification information contained in the data 132. In some embodiments, the determination may be made by time information (for example, data collection start time) contained in the data 132. For example, for a data collection protocol in which the measurement under stress is performed earlier, the data 132 can be identified as the prescan data when the data collection start time indicated by the data 132 is between the data collection completion time of the stress data 130 and the data collection start time of the rest data 134. For a data collection protocol in which the measurement at rest is performed earlier, the data 132 can be identified as the prescan data when the data collection start time indicated by the data 132 is between the data collection completion time of the rest data 134 and the data collection start time of the stress data 130.

In step 330, the alignment of the stress data 130, the prescan data 132, and the rest data 134 is performed. In other words, positions or sizes are adjusted in such a manner that the positions or sizes of myocardial images made from these pieces of data will coincide with each other. The processing may be performed through execution of the alignment program 122 by the CPU 102. The myocardial blood flow increase rate calculation program 120 may be executed by the CPU 102 calling the alignment program 122 in step 330.

For a data collection protocol in which the measurement under stress is performed earlier, the alignment is preferably performed on the basis of the rest data 134. For a data collection protocol in which the measurement at rest is performed earlier, the alignment is preferably performed on the basis of the stress data 130.

Step 335 is optional processing. In this step, the stress data 130 after alignment and the rest data 134 after alignment are each subjected to myocardial contour extraction. The processing in step 335 is particularly required when processing 600 or processing 700 is performed as an embodiment of step 345.

The processing in step 335 may be performed through execution of the contour extraction/volume calculation program 124 by the CPU 102. As described above, some algorithms and software for myocardial contour extraction are known, and such an algorithm is disclosed by the present applicant in PCT International Publication (WO2013/047496A1), for example. The program instructions included in the contour extraction/volume calculation program 124 may be configured to use the algorithm to extract the myocardial contour.

In some embodiments, the contour extraction/volume calculation program 124 may be configured to use the extracted contour to calculate the myocardial volume. For example, the number of pixels present between the intima and the adventitia of the extracted myocardium may be multiplied by a pixel-volume conversion factor (for example, volume per pixel) to give a myocardial volume.

In some embodiments, the prescan data 132 may be subjected to the myocardial contour extraction. In the prescan, however, the data collection time may be short, and the data collection is performed without the administration of a radiopharmaceutical agent. The pixel value (radiation count value) of each pixel in the prescan data 132 is thus low in many cases. On this account, the myocardial contour extraction of the prescan data 132 is failed in some cases. In such a case, the myocardial contour information of the prescan data 132 may be considered to be the same as the myocardial contour information of the stress data 130 or the rest data 134. In particular, the myocardial contour information of the prescan data 132 may be considered to be the same as the myocardial contour information of later-collected data of the stress data 130 and the rest data 134.

Step 340 is also an optional step. In some embodiments, all the pixels or all the myocardial pixels of the stress data 130 and the rest data 134 may be used to calculate a myocardial blood flow increase rate. In some embodiments, part of the pixels can be used to calculate a myocardial blood flow increase rate. For example, the data 130 to the data 134 can be converted into array data or polar maps (polar coordinate display), which are often used in the technical field of the present application, and each pixel can be used to calculate a myocardial blood flow increase rate. In other words, array data or polar maps for a myocardial blood flow increase rate may be prepared. The array data is prepared as follows: each short axis tomogram in a certain range is radially scanned at every certain angle from the image center to determine a maximum pixel value, and the determined values are used to prepare a two-dimensional map in which one axis represents positions of the short axis tomograms and the other axis represents angles from the image center. The polar maps are prepared as follows: each short axis tomogram in a certain range is radially scanned at every certain angle from the image center to determine a maximum pixel value, and the determined values are plotted at concentric polar coordinates.

By converting the data 130 to the data 134 into array data or polar maps, the processing load in the next step 345 can be reduced, and the visibility of the results can be improved.

When step 340 is performed, each of the stress data 130, the prescan data 132, and the rest data 134 is converted into array data or a polar map. It should be understood that when the conversion is performed, each of the stress data 130, the prescan data 132, and the rest data 134 has been converted into array data or a polar map in the following description.

In step 345, a myocardial blood flow increase rate is calculated. The step typically includes four embodiments. With reference to FIGS. 4 to 7, each embodiment will be described next.

Figure 3:
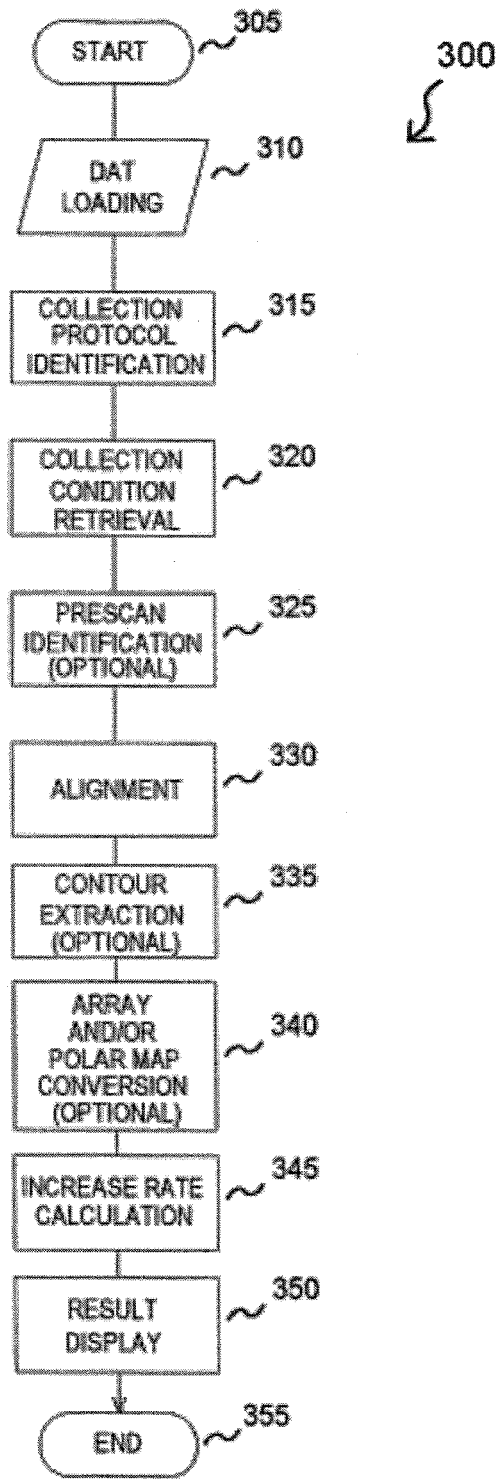
FIG. 3 is a flowchart for explaining a preferred example of the processing for calculation of a myocardial blood flow increase rate.
Figure 4:
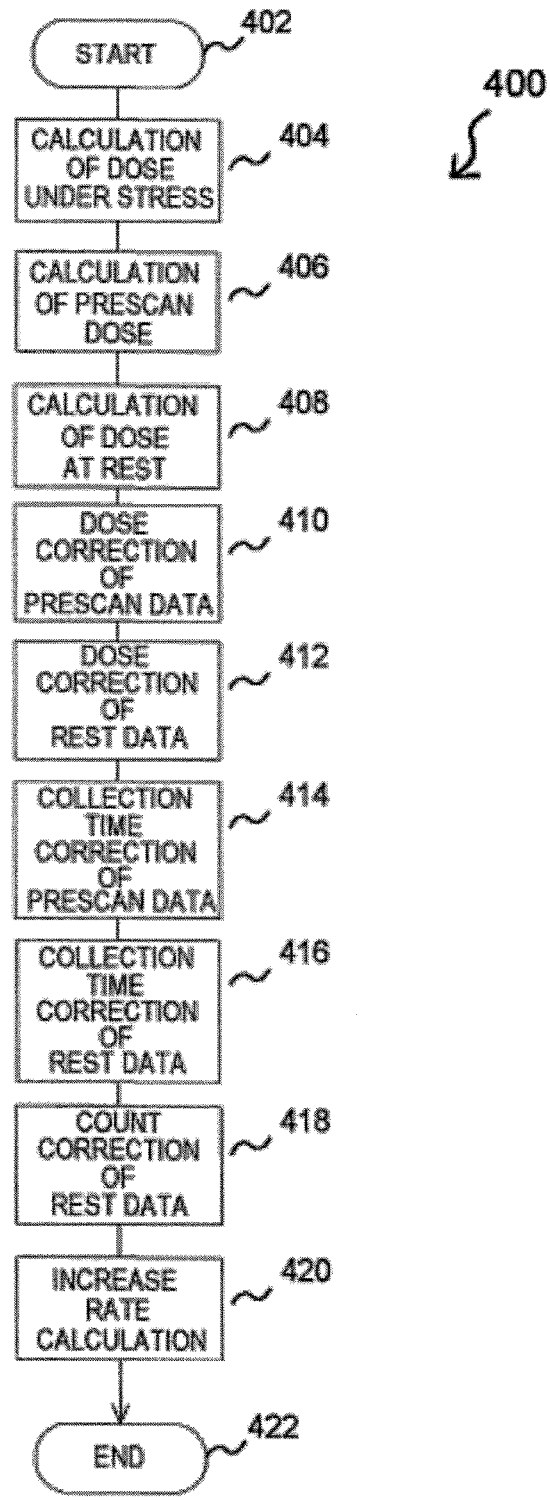
FIG. 4 is a flowchart for explaining a specific example of step 345 in FIG. 3.

FIG. 4 is a flowchart for explaining processing 400 that is an embodiment of step 345 in FIG. 3. As with the processing illustrated in FIG. 3 and FIGS. 5 to 7, the processing 400 is processing for calculating a myocardial blood flow increase rate and is performed by the system 100 in which the myocardial blood flow increase rate calculation program 120 is executed by the CPU 102.

The processing 400 is performed when a data collection protocol is identified in step 315 as the protocol in which the measurement under stress is performed before the measurement at rest. The processing 400 is performed when a myocardial blood flow increase rate is calculated without SUV conversion of the image data 130 or the data 134, which is described later.

Step 402 indicates the start of processing. In step 404, the radiation dose administered to a subject for the measurement under stress (dose under stress) is calculated. The information required for the calculation of an administered radiation dose is the following information.

A radiation dose measured before administration of a radiopharmaceutical agent to a subject (radiation dose before administration)

The measurement date and time of a radiation dose before administration

The date and time at the start of data collection

A radiation dose measured after administration of the radiopharmaceutical agent to the subject (radiation dose after administration)

The measurement date and time of the radiation dose after administration

The half-life of a tracer contained in the radiopharmaceutical agent

In the present example, the information is retrieved in step 320 and is stored in the collection condition file 131. The system 100 may thus retrieve the information from the collection condition file 131 in step 404.

Subsequently, the dose under stress is calculated in accordance with the following equations:

Decay time 1 (seconds)=|Measurement date and time of radiation dose before administration−Date and time at start of data collection|

Decay time 2 (seconds)=|Measurement date and time of radiation dose after administration−Date and time at start of data collection|

Decay coefficient=LN (2.0)/Half-life (seconds) (LN: natural logarithm to the base $e$)

Dose under stress={Radiation dose before administration×Exp (−Decay coefficient×Decay time 1)}−{(Radiation dose after administration×Exp (−Decay coefficient×Decay time 2)}.

In subsequent step 406, the radiation dose administered to the subject for prescan (prescan dose) is calculated. The information required for the calculation is the following information.

A radiation dose measured before administration of a radiopharmaceutical agent to the subject under stress (radiation dose before administration)

The measurement date and time of a radiation dose before administration

The date and time at the start of data collection

A radiation dose measured after administration of the radiopharmaceutical agent to the subject under stress (radiation dose after administration)

The measurement date and time of a radiation dose after administration

The half-life of a tracer contained in the radiopharmaceutical agent

In other words, the information required is the same as that fox calculation of a dose under stress.

As described above, no radiopharmaceutical agent is administered for only prescan. As described in the section of the protocol in which the measurement under stress is performed earlier in FIG. 2, the prescan in the embodiment is radiation data collection performed after the measurement under stress without the administration of a radiopharmaceutical agent. The above-described information is thus the same as that on the measurement under stress except the date and time at the start of data collection. In other words, the information is the same as that used in step 404. Only for the date and time at the start of data collection, the information of the date and time at the start of prescan data collection is needed.

In some embodiments, the information other than the date and time at the start of data collection, of the above-described information may be retrieved from the collection condition file 131 for the stress data 130. The date and time at the start of data collection may be retrieved from the collection condition file 133 for the prescan data 132 (the date and time at the start of prescan data collection has been retrieved in step 320). In some embodiments, the system 100 may be configured to automatically copy the information other than the date and time at the start of data collection from the collection condition file 131 into the collection condition file 133. In such a case, the system 100 may be configured to retrieve all the information from the collection condition file 133 in this step.

After the retrieval of the information, the system 100 calculates a prescan dose in a similar manner to that under stress, in accordance with the equations.

Decay time 1 (seconds)=|Measurement date and time of radiation dose before administration−Date and time at start of data collection|

Decay time 2 (seconds)=|Measurement date and time of radiation dose after administration−Date and time at start of data collection|

Decay coefficient=LN (2.0)/Half-life (seconds) (LN: natural logarithm to the base $e$)

Prescan dose={Radiation dose before administration×Exp (−Decay coefficient×Decay time 1)}−{Radiation dose after administration×Exp (−Decay coefficient×Decay time 2)}.

In step 408, the radiation dose administered to the subject at rest (dose at rest) is calculated. The information required for the calculation is also the same as that when the dose under stress is calculated, and is the following information.

A radiation dose measured before administration of a radiopharmaceutical agent to the subject at rest (radiation dose before administration)

The measurement date and time of a radiation dose before administration

The date and time at the start of data collection radiation dose measured after administration of the radiopharmaceutical agent to the subject at rest (radiation dose after administration)

The measurement date and time of a radiation dose after administration

The half-life of a tracer contained in the radiopharmaceutical agent

In the present example, the information has been retrieved in step 320 and has been stored in the collection condition file 135. The system 100 may thus retrieve the information from the collection condition file 135 in this step.

The system 100 may be configured to then calculate a dose at rest in a similar manner to that under stress, in accordance with the equations.

Decay time 1 (seconds)=|Measurement date and time of radiation dose before administration−Date and time at start of data collection|

Decay time 2 (seconds)=|Measurement date and time of radiation dose after administration−Date and time at start of data collection|

Decay coefficient=LN (2.0)/Half-life (seconds) (LN: natural logarithm to the base $e$)

Dose at rest={Radiation dose before administration×Exp (−Decay coefficient×Decay time 1)}−{Radiation dose after administration×Exp (−Decay coefficient×Decay time 2)}.

In step 410, each pixel value of the prescan data 132 is multiplied by the following correction factor to perform dose correction:

Dose correction factor for prescan data=Dose under stress/Prescan dose.

In step 412, each pixel value of the rest data 134 is multiplied by the following correction factor to perform dose correction:

Dose correction factor for rest data=Dose under stress/Dose at rest.

In step 414, each pixel value of the prescan data 132 after dose correction is multiplied by the following correction factor to perform collection time correction:

Collection time correction factor for prescan data=Stress data collection time/Prescan data collection time.

In the present example, the stress data collection time and the prescan data collection time have been retrieved in step 320 and have been stored in the collection condition files 131 and 133, respectively. The system 100 may thus be configured to retrieve the information about the stress data collection time and the prescan data collection time from these files and to calculate the collection time correction factor for prescan data.

In step 416, each pixel value of the rest data 134 after dose correction is multiplied by the following correction factor to perform collection time correction:

Collection time correction factor for rest data=Stress data collection time/Rest data collection time.

In the present example, the rest data collection time has been retrieved in step 320 and has been stored in the collection condition file 135, and thus the system 100 may be configured to retrieve information required from the collection condition file 135 and to calculate the collection time correction factor for rest data.

In step 418, the prescan data 132 after dose correction and collection time correction is used to perform count correction of the rest data 134 after dose correction and collection time correction. The correction is performed by subtracting, from the pixel value of each pixel of the rest data 134 after the correction (dose correction (step 412) and collection time correction (step 416)), the pixel value of the pixel at a corresponding position in the prescan data. 132 after the correction. By performing the count correction, the effect of a radiopharmaceutical agent administered under stress is eliminated from the rest data 134.

In step 420, the stress data 130 and the rest data 134 after count correction are used to calculate a myocardial blood flow increase rate. The myocardial blood flow increase rate of a pixel ij ($IncMap_{ij}$) is determined from the pixel, value of each pixel in the stress data 130 ($Stress_{ij}$) and the pixel value of the pixel at a corresponding position in the rest data 134 after count correction ($Rest_{ij}$) in accordance with the equation:

$$IncMap_{ij}[\%]=(Stress_{ij}-Rest_{ij})/(Rest_{ij})\times 100.$$

The calculated increase rate data may be stored as increase rate data 140 in the mass storage unit 106, for example (see FIG. 1). The increase rate data 140 can be three-dimensional image data in which the pixel value of each pixel represents an increase rate, for example. When step 340 in FIG. is performed, the increase rate data may be two-dimensional array data or a two-dimensional polar map in which the pixel value of each pixel represents an increase rate.

By performing the count correction in step 418, the effect of a radiopharmaceutical agent administered under stress is eliminated from the rest data 134. Accordingly, the pixel value of each pixel in the rest data 134 after the correction reflects cardiac functions at rest more correctly. Calculation using such data enables determination of myocardial blood flow increase rates more correctly than in the related art.

Step 422 indicates the end of the processing.

Figure 5:
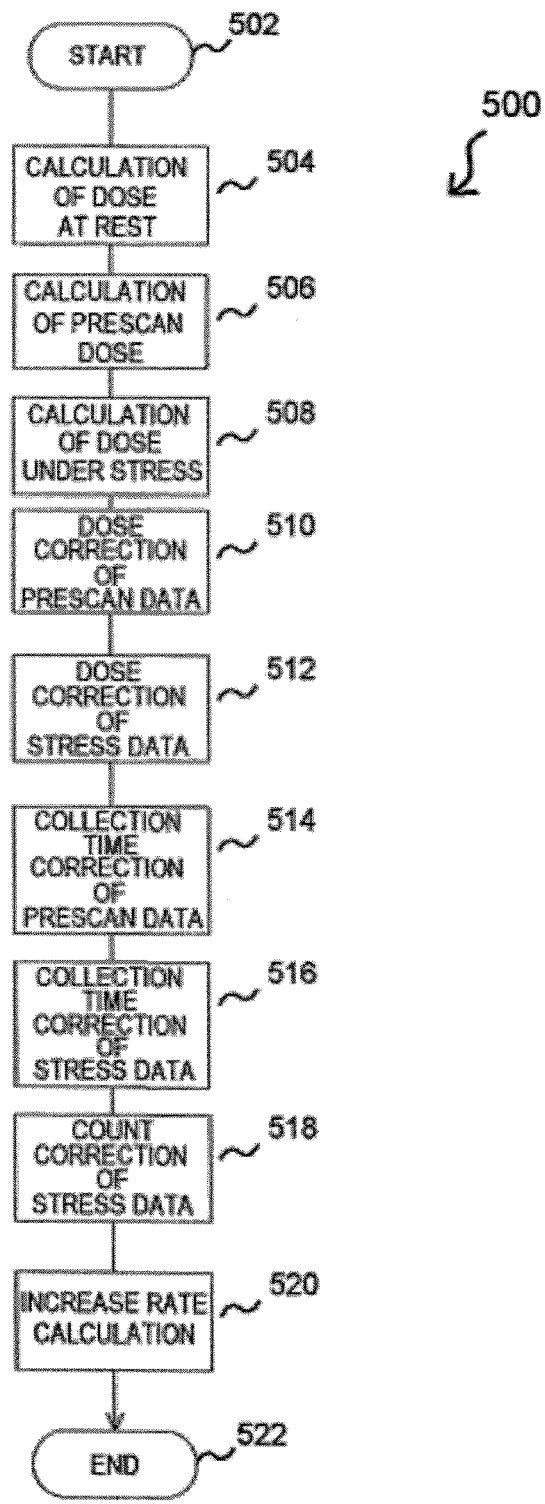
FIG. 5 is a flowchart for explaining another specific example of step 345 in FIG. 3.

FIG. 5 is a flowchart for explaining processing 500 that is an embodiment of step 345 in FIG. 3 and is for the calculation of a myocardial blood flow increase rate. The processing 500 is performed when a data collection protocol is identified in step 315 as the protocol in which the measurement at rest is performed before the measurement under stress. The processing 500 is performed when a myocardial blood flow increase rate is calculated without SUV conversion of the image data 130 or the data 134, which is described later.

Step 502 indicates the start of processing. In step 504, the radiation dose administered to a subject in the measurement at rest (dose at rest) is calculated. The information required for the calculation of an administered radiation dose is the following information.

A radiation dose measured before administration of a radiopharmaceutical agent to a subject (radiation dose before administration)

The measurement date and time of a radiation dose before administration

The date and time at the start of data collection

A radiation dose measured after administration of the radiopharmaceutical agent to the subject (radiation dose after administration)

The measurement date and time of a radiation dose after administration

The half-life of a tracer contained in the radiopharmaceutical agent

In the present example, the information has been retrieved in step 320 and has been stored in the collection condition file 135. The system 100 may thus retrieve the information from the collection condition file 135 in step 502.

Subsequently, a dose at rest is calculated in accordance with the equations.

Decay time 1 (seconds)=|Measurement date and time of radiation dose before administration−Date and time at start of data collection|

Decay time 2 (seconds)=|Measurement date and time of radiation dose after administration−Date and time at start of data collection|

Decay coefficient=LN (2.0)/Half-life (seconds) (LN: natural logarithm to the base $e$)

Dose at rest={Radiation dose before administration× Exp (−Decay coefficient×Decay time 1)}−{Radiation dose after administration×Exp (−Decay coefficient×Decay time 2)}.

In subsequent step 506, the radiation dose administered to the subject for prescan (prescan dose) is calculated. The information required for the calculation is the following information.

A radiation dose measured before administration of a radiopharmaceutical agent to the subject in the nuclear medicine image data collection at rest (radiation dose before administration)

The measurement date and time of a radiation dose before administration

The date and time at the start of data collection

A radiation dose measured after administration of the radiopharmaceutical agent to the subject in the nuclear medicine image data collection at rest (radiation dose after administration)

The measurement date and time of a radiation dose after administration

The half-life of a tracer contained in the radiopharmaceutical agent

In other words, the information required is the same as that for calculation of a dose at rest.

As described above, no radiopharmaceutical agent is administered for only prescan. As described in the section of the protocol in which the measurement at rest is performed earlier in FIG. 2, the prescan in the embodiment is radiation data collection performed after the measurement at rest without the administration of a radiopharmaceutical agent. Hence, the above-described information is the same as that on the measurement at rest except the date and time at the start of data collection. In other words, the information is the same as that used in step 504. Only for the date and time at the start of data collection, the information of the date and time at the start of prescan data collection is needed.

In some embodiments, the information other than the date and time at the start of data collection, of the above-described information may be retrieved from the collection condition file 135 for the rest data 134. The date and time at the start of data collection may be retrieved from the collection condition file 133 for the prescan data 132 (the date and time at the start of prescan data collection has been retrieved in step 320). In some embodiments, the system 100 may be configured to automatically copy the information other than the date and time at the start of data collection from the collection condition file 135 into the collection condition file 133. In such a case, the system 100 may be configured to retrieve all the information from the collection condition file 133 in this step.

After the retrieval of the information, the system 100 calculates a prescan dose in a similar manner to that at rest, in accordance with the equations.

> Decay time 1 (seconds)=|Measurement date and time of radiation dose before administration−Date and time at start of data collection|
>
> Decay time 2 (seconds)=|Measurement date and time of radiation dose after administration−Date and time at start of data collection|
>
> Decay coefficient=LN (2.0)/Half-life (seconds) (LN: natural logarithm to the base $e$)
>
> Prescan dose={Radiation dose before administration×Exp (−Decay coefficient×Decay time 1)}−{Radiation dose after administration×Exp (−Decay coefficient×Decay time 2)}.

In step 508, the radiation dose administered to the subject under stress (dose under stress) is calculated. The information required for the calculation is also the same as that when the dose at rest is calculated, and is the following information.

A radiation dose measured before administration of a radiopharmaceutical agent to the subject (radiation dose before administration)

The measurement date and time of a radiation dose before administration

The date and time at the start of data collection

A radiation dose measured after administration of the radiopharmaceutical agent to the subject (radiation dose after administration)

The measurement date and time of a radiation dose after administration

The half-life of a tracer contained in the radiopharmaceutical agent

In the present example, the information has been retrieved in step 320 and has been stored in the collection condition file 131. The system 100 may thus retrieve the information from the collection condition file 131 in this step.

The system 100 may be configured to then calculate a dose under stress in a similar manner to that at rest, in accordance with the equations.

> Decay time 1 (seconds)=|Measurement date and time of radiation dose before administration−Date and time at start of data collection|
>
> Decay time 2 (seconds)=|Measurement date and time of radiation dose after administration−Date and time at start of data collection|
>
> Decay coefficient=LN (2.0)/Half-life (seconds) (LN: natural logarithm to the base $e$)
>
> Dose under stress={Radiation dose before administration×Exp (−Decay coefficient×Decay time 1)}−{Radiation dose after administration×Exp(−Decay coefficient×Decay time 2)}.

In step 510, each pixel value of the prescan data 132 is multiplied by the following correction factor to perform dose correction:

> Dose correction factor for prescan data=Dose at rest/Prescan dose.

In step 512, each pixel value of the stress data 130 is multiplied by the following correction factor to perform dose correction:

> Dose correction factor for stress data=Dose at rest/Dose under stress.

In step 514, each pixel value of the prescan data 132 after dose correction is multiplied by the following correction factor to perform collection time correction:

> Collection time correction factor for prescan data=Rest data collection time/Prescan data collection time.

In the present example, the rest data collection time and the prescan data collection time have been retrieved in step 320 and have been stored in the collection condition files 135 and 133, respectively. The system 100 may thus be configured to retrieve the information about the rest data collection time and the prescan data collection time from these files and to calculate a collection time correction factor for prescan data.

In step 516, each pixel value of the stress data 130 after dose correction is multiplied by the following correction factor to perform collection time correction:

> Collection time correction factor for stress data=Rest data collection time/Stress data collection time.

In the present example, the stress data collection time has been retrieved in step 320 and has been stored in the collection condition file 131, and thus the system 100 may be configured to retrieve information required from the collection condition file 131 and to calculate the collection time correction factor for stress data.

In step 518, the prescan data 132 after dose correction and collection time correction is used to perform count correction of the stress data 130 after dose correction and collection time correction. The correction is performed by subtracting, from the pixel value of each pixel of the stress data 130 after dose correction (step 512) and collection time correction (step 516), the pixel value of the pixel at a corresponding position in the prescan data 132 after the correction. By performing the count correction, the effect of a radiopharmaceutical agent administered for the measurement at rest is eliminated from the stress data 130.

In step 520, the stress data 130 after count correction and the rest data 134 are used to calculate a myocardial blood flow increase rate. The myocardial blood flow increase rate of a pixel ij ($IncMap_{ij}$) is determined from the pixel value of each pixel in the stress data 130 after count correction ($Stress_{ij}$) and the pixel value of the pixel at a corresponding position in the rest data 134 after count correction ($Rest_{ij}$) in accordance with the equation:

> $IncMap_{ij}[\%]=(Stress_{ij}-Rest_{ij})/(Rest_{ij})\times 100$.

The calculated increase rate data may be stored as increase rate data 140 in the mass storage unit 106, for example (see FIG. 1). The increase rate data 140 can be three-dimensional image data in which the pixel value of each pixel represents an increase rate, for example. When step 340 in FIG. is performed, the increase rate data may be two-dimensional array data or a two-dimensional polar map in which the pixel value of each pixel represents an increase rate.

By performing the count correction in step 518, the effect of a radiopharmaceutical agent administered at rest is eliminated from the stress data 130. Accordingly, the pixel value of each pixel in the stress data 130 reflects cardiac functions under stress more correctly. Calculation using such data enables determination of myocardial blood flow increase rates more correctly than in the related art.

Step 522 indicates the end of the processing.

Figure 6:
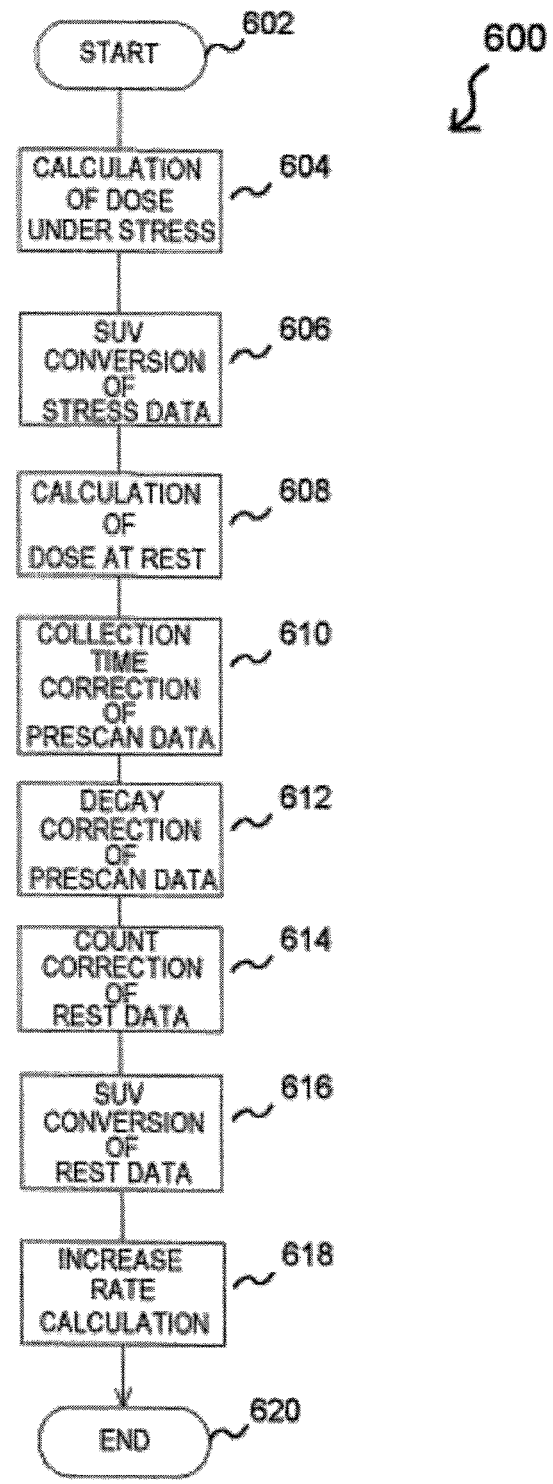
FIG. 6 is a flowchart for explaining still another specific example of step 345 in FIG. 3.

FIG. 6 is a flowchart for explaining processing 600 that is an embodiment of step 345 in FIG. 3 and is for the calculation of a myocardial blood flow increase rate. The processing 600 is performed when a data collection protocol is identified in step 315 as the protocol in which the measurement under stress is performed before the measurement at rest. The processing 600 is performed when the image data 130 and the data 134 are subjected to characteristic SUV conversion disclosed in the present application and then a myocardial blood flow increase rate is calculated.

Step 602 indicates the start of processing. In step 604, the radiation dose administered to a subject in the measurement under stress (dose under stress) is calculated. The calculation method of the dose under stress is the same as in step 404 described for the processing 400 in FIG. 4 and thus is not described.

In step 606, the pixel value of each pixel in the stress data 130 is converted into an SUV. The existing SUV conversion uses the body weight of a subject for normalization. In contrast, the SUV conversion of the present embodiment is performed in accordance with equation 1.

SUV=Tissue radioactivity concentration/(Administered radiation dose/Myocardial weight) [Equation 1]

Each parameter will be briefly described below.

Tissue radioactivity concentration: the value obtained by multiplying the pixel value of each pixel in the stress data 130 by a becquerel calibration factor (BCF). The BCF is a factor for converting a radiation count value into a radiodensity (for example, Bq/ml). In the present example, the BCF has been retrieved in step 320. In an embodiment in which the pixel value of each pixel in stress data 130 represents a tissue radioactivity concentration, the pixel value is not multiplied by the BCF, but the pixel value itself can be used as the tissue radioactivity concentration.

Administered radiation dose: in this step, it is a radiation dose administered to a subject in the measurement under stress. In other words, it is the dose under stress determined in step 604.

Myocardial weight: it is calculated on the basis of the myocardium contour data of the stress data obtained in step 335. For example, the number of pixels presents between the intima and the adventitia of the extracted myocardium may be multiplied by a pixel-volume conversion factor to give a myocardial volume, and the myocardial volume may be multiplied by a myocardial volume-myocardial weight conversion factor (density factor) to give a myocardial weight. The density factor can be known literature data and may be 1.05, for example. The myocardial weight may be calculated in step 335 or in the present step. In some embodiments, the myocardial weight calculation algorithm may be installed in the contour extraction/volume calculation program 124 or in the myocardial blood flow increase rate calculation program 120. The calculated myocardial weight may be stored in the main memory unit 102 or the mass storage unit 106. In some embodiments, the myocardial weight may be stored in a register of the CPU 102.

The stress data after conversion of the pixel value of each pixel into an SUV may be stored as stress SUV data 150 in the mass storage unit 106, for example (see FIG. 1).

The BCF can be determined by a known method. For example, a nuclear medicine image of a vial (or a syringe) containing a radiopharmaceutical agent having a known total radioactivity can be taken, and the BCF can be calculated in accordance with the following equation:

BCF=Decay-corrected total radioactivity (Bq)/(Total count of all slices/Collection time (seconds)).

To determine the BCF from the data obtained using a cylindrical phantom, the following equations can be used:

Volume factor=Average count value per slice/(Volume of single pixel×Collection time (seconds))

BCF=Decay-corrected total radioactivity (Bq)/(Phantom volume×Volume factor).

In some embodiments, the BCF may be subjected to collection time correction. The collection time correction may be performed by multiplying {Volume of single pixel [$cm^3$]/Collection time [sec]} by BCF, for example.

In step 608, the radiation dose administered to the subject in the measurement at rest (dose at rest) is calculated. The calculation method of the dose at rest is the same as in step 408 described for the processing 400 in FIG. 4 and thus is not described.

In step 610, each pixel value of the prescan data 132 is multiplied by the following correction factor to perform collection time correction:

Collection time correction factor=Rest data collection time/Prescan data collection time.

In the present example, the rest data collection time and the prescan data collection time have been retrieved in step 320 and have been stored in the collection condition files 135 and 133, respectively. The system 100 may thus be configured to retrieve the information about the rest data collection time and the prescan data collection time from these files and to calculate the collection time correction factor.

In step 612, each pixel value of the prescan data 132 after collection time correction is multiplied by the decay correction factor determined as follows to perform decay correction:

Decay time (seconds)=Date and time at start of prescan data collection−Date and time at start of rest data collection, Decay coefficient=LN (2.0)/Half-life (seconds) of tracer (LN: natural logarithm to the base $e$), and Decay correction factor=Exp (Decay coefficient× Decay time).

In step 614, the prescan data 132 after collection time correction and decay correction is used to perform count correction of the rest data 134. The correction is performed by subtracting, from the pixel value of each pixel of the rest data 134, the pixel value of the pixel at a corresponding position in the prescan data 132 after correction. By performing the count correction, the effect of a radiopharmaceutical agent administered under stress is eliminated from the rest data 134.

In step 616, the pixel value of each pixel in the rest data 134 after count correction is converted into an SUV. The conversion equation is the same as equation 1 described above. However, the "tissue radioactivity concentration" in the equation is the pixel value in the rest data 134 and is obtained by multiplying the pixel value after the count correction described in step 614 by the above-described BCF. In the equation, the "administered radiation dose" is the dose at rest determined in step 608. In the equation, the "myocardial weight" is calculated on the basis of myocardial contour data of the rest data (for example, the data obtained in step 335).

The rest data after conversion of the pixel value of each pixel into an SUV may be stored as rest SUV data 152 in the mass storage unit 106, for example (see FIG. 1).

In step 618, the stress SUV data 150 and the rest SUV data 152 are used to calculate a myocardial blood flow increase rate. The myocardial blood flow increase rate of a pixel ij (IncMap$_{ij}$) is determined from the pixel value of each pixel in the stress SUV data 150 (Stress_SUV$_{ij}$) and the pixel value of the pixel at a corresponding position in the rest SUV data 152 (Rest_SUV$_{ij}$) in accordance with the equation:

$$\text{IncMap}_{ij}[\%-]=(\text{Stress\_SUV}_{ij}-\text{Rest\_SUV}_{ij})/(\text{Rest\_SUV}_{ij})\times 100.$$

The calculated increase rate data may be stored as increase rate data 140 in the mass storage unit 106, for example (see FIG. 1). The increase rate data 140 can be three-dimensional image data in which the pixel value of each pixel represents an increase rate, for example. When step 340 in FIG. 3 is performed, the increase rate data may be two-dimensional array data or a two-dimensional polar map in which the pixel value of each pixel represents an increase rate.

In the present example, the weight of the myocardium in which a tracer is accumulated is used as a standard to normalize myocardial nuclear medicine image data. The normalized value thus reflects actual conditions of cardiac functions more correctly than in the related art. Such normalized values are used to calculate myocardial blood flow increase rates, and thus the comparability of myocardial blood flow increase rates is improved as compared with the related art. In other words, the present technique facilitates the comparison with past examination results or the comparison with examination results of another subject. In some embodiments, the myocardial volume can be used to perform normalization in place of the myocardial weight. Alternatively, another index relating to the heart size can be used to perform normalization.

By performing the count correction in step 614, the effect of a radiopharmaceutical agent administered under stress is eliminated from the rest data 134. Accordingly, the pixel value of each pixel in the rest data 134 reflects cardiac functions at rest more correctly. Calculation using such data enables determination of SUVs and myocardial blood flow increase rates more correctly than in the related art.

Step 620 indicates the end of the processing.

Figure 7:
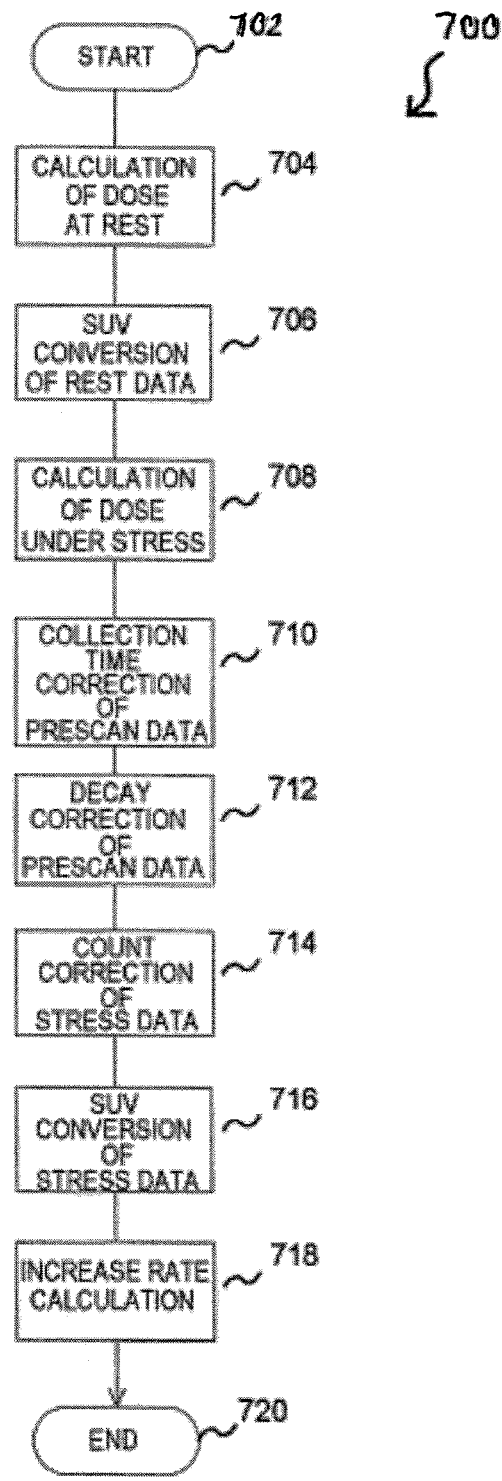
FIG. 7 is a flowchart for explaining still another specific example of step 345 in FIG. 3.

FIG. 7 is a flowchart for explaining processing 700 that is an embodiment of step 345 in FIG. 3 and is for the calculation of a myocardial blood flow increase rate. The processing 700 is performed when a data collection protocol is identified in step 315 as the protocol in which the measurement at rest is performed before the measurement under stress. The processing 700 is performed when the image data 130 and the image data 134 are subjected to characteristic SUV conversion disclosed in the present application and then a myocardial blood flow increase rate is calculated.

Step 702 indicates the start of processing. In step 704, the radiation dose administered to a subject in the measurement at rest (dose at rest) is calculated. The calculation method of the dose at rest is the same as in step 408 described for the processing 400 in FIG. 4 and thus is not described.

In step 706, the pixel value of each pixel in the rest data 130 is converted into an SUV. The conversion equation is the same as equation 1 disclosed in the section of step 606. However, the "tissue radioactivity concentration" in the equation is obtained by multiplying the pixel value in the rest data 134 by the BCF. In the equation, the "administered radiation dose" is the dose at rest determined in step 704. In the equation, the "myocardial weight" is calculated on the basis of myocardial contour data of the rest data.

The rest data after conversion of the pixel value of each pixel into an SUV may be stored as rest SUV data 152 in the mass storage unit 106, for example (see FIG. 1).

In step 708, the radiation dose administered to a subject in the measurement under stress (dose under stress) is calculated. The calculation method of the dose under stress is the same as in step 404 described for the processing 400 in FIG. 4 and thus is not described.

In step 710, each pixel value of the prescan data 132 is multiplied by the following correction factor to perform collection time correction:

Collection time correction factor=Stress data collection time/Prescan data collection time.

In the present example, the stress data collection time and the prescan data collection time have been retrieved in step 320 and have been stored in the collection condition files 131 and 133, respectively. The system 100 may thus be configured to retrieve the information about the stress data collection time and the prescan data collection time from these files and to calculate the collection time correction factor mentioned above.

In step 712, each pixel value of the prescan data 132 after collection time correction is multiplied by the decay correction factor determined as follows to perform, decay correction:

Decay time (seconds)=Date and time at start of prescan data collection−Date and time at start of stress data collection, Decay coefficient=LN (2.0)/Half-life (seconds) of tracer (LN: natural logarithm to the base *e*), and Decay correction factor=Exp (Decay coefficient× Decay time).

In step 714, the prescan data 132 after collection time correction and decay correction is used to perform count correction of the stress data 130. The correction is performed by subtracting, from the pixel value of each pixel of the stress data 130, the pixel value of the pixel at a corresponding position in the prescan data 132 after correction. By performing the count correction, the effect of a radiopharmaceutical agent administered in the measurement at rest is eliminated from the stress data 130.

In step 716, the pixel value of each pixel in the stress data 130 after count correction is converted into an SUV. The conversion equation is the same as equation 1 above. However, the "tissue radioactivity concentration" in the equation is the pixel value in the stress data 130 and is obtained by multiplying the pixel value after the count correction described in step 714 by the above-described BCF. In the equation, the "administered radiation dose" is the dose under stress determined in step 708. In the equation, the "myocardial weight" is calculated on the basis of myocardial contour data of the stress data as described in step 606.

The stress data after conversion of the pixel value of each pixel into an SUV may be stored as stress SUV data 152 in the mass storage unit 106, for example (see FIG. 1).

In step 718, the stress SUV data 150 and the rest SUV data 152 are used to calculate a myocardial blood flow increase rate. The processing in this step is the same as in step 618, and thus is not described.

In the present example, the weight or the volume of the myocardium in which a tracer is accumulated is used as a standard to normalize myocardial nuclear medicine image data. The normalized value thus reflects actual conditions of cardiac functions more correctly than in the related art. Such normalized values are used to calculate myocardial blood flow increase rates, and thus the comparability of myocardial blood flow increase rates is improved as compared with the related art. In other words, the present technique facilitates the comparison with past examination results or the comparison with examination results of another subject.

By performing the count correction in step 714, the effect of a radiopharmaceutical agent administered in the measurement at rest is eliminated from the stress data 130. Accordingly, the pixel value of each pixel in the stress data 130 reflects cardiac functions at stress more correctly. Calculation using such data enables determination of SUVs and myocardial blood flow increase rates more correctly than in the related art.

Step 720 indicates the end of the processing.

Embodiments of step 345 in FIG. 3 have been described.

In each embodiment, the data obtained from measurement performed later between the measurement under stress and the measurement at rest is corrected by the data obtained through prescan. This corrects the effect of radioactivity that has been administered in the earlier measurement, remaining in the data obtained through the measurement performed later. This correction improves the validity of data and increases the reliability of the myocardial blood flow increase rate to be calculated. This technique can markedly shorten the time interval required between the measurement under stress and the measurement at rest as compared with the related art, and can reduce the measurement burden on both an operator and a subject.

In the embodiment exemplified in the processing 600 or the processing 700, the pixel values of nuclear medicine image data are converted into SUVs using the myocardial weight, which is the normalization on a more appropriate supposition for the accumulation of a tracer than in the related art, resulting in improved validity or reliability when pieces of data are compared between different measurement dates and times or between different subjects.

The flowchart in FIG. 3 will be described again. In step 350, the calculation result of the myocardial blood flow increase rate is displayed. The display may be made in various manners. For example, when the increase rate data 140 storing the results is three-dimensional image data in which the pixel value of each pixel represents an increase rate, calculated myocardial blood flow increase rates may be displayed as differences in brightness or color tone where short axis tomograms are displayed side by side. Such a displaying manner enables detailed observation of how the myocardial blood flow increase rate changes at respective sliced positions.

For example, when the increase rate data 140 storing the results is two-dimensional array data or a two-dimensional polar map in which the pixel value of each pixel represents an increase rate, the result can be displayed as the two-dimensional array or the two-dimensional polar map without any processing. The variation of the myocardial blood flow increase rate with positions can be easily observed in a single chart. In some embodiments, the increase rate data 140 may be displayed together with the stress data 130 or the rest data 134 converted into two-dimensional array data or a two-dimensional polar map. Alternatively, the increase rate data 140 may be displayed together with the stress SUV data 150 or the rest SUV data 152 converted into two-dimensional array data or a two-dimensional polar map. In such a case, the arrangement of maps in the order of a map at rest, a map under stress, and an increase rate map facilitates the observation of increase rates under stress, which is advantageous.

The invention of the present application has been specifically described with reference to preferred examples. The description and the attached drawings are not intended to limit the scope of the invention of the present application, but are intended to satisfy the requirements of the law. Embodiments of the invention of the present application include various variations in addition to the above-exemplified embodiments. For example, various numerical values shown in the description or the drawings are illustrative values and are not intended to limit the scope of the invention. Individual features included in the various examples that have been described in the description or the drawings are not limited to usage with examples in which these features are explicitly explained to be included, but may be used in combination with other examples that have been described herein or various specific examples that have not been described. In particular, the processes presented in the flowcharts do not necessarily need to be performed in the described order. According to the preference of an executor, the processes may be performed in a changed order or in parallel, or as a plurality of blocks integrally implemented, or in a loop as appropriate. These variations are all included in the scope of the invention disclosed in the present application. The form of implementing processes does not limit the scope of the invention. The order of the description of the processes defined in the claims does not necessarily specify the mandatory order of the processes. For example, an embodiment specifying a different order of the processes and an embodiment that executes the processes in a loop are also included in the scope of the invention according to the claims.

For example, an embodiment of the myocardial blood flow increase rate calculation program 120 can include a single program, a program group including a plurality of independent programs, and a program integrated with all or part of the alignment program 122 or the contour extraction/volume calculation program 124. A program can be installed in various manners, which are well known, and all the various manners are included in the scope of the invention disclosed in the present application.

It should be noted that novel SUVs disclosed in the present application are not solely for deriving myocardial blood flow increase rates as disclosed in the present application. The novel SUV disclosed in the present application is characterized using the weight or volume of a myocardium for normalization, and thus the SUV of the present application can be used in all the fields in which the normalization is appropriate, such as various nuclear medicine examinations of the heart. It should be noted that the applicant claims to possess the right to have a patent granted on all the embodiments not deviating from the spirit of the invention regardless of whether a patent is claimed in the current set of attached claims.

The invention claimed is:

1. A method of processing myocardial nuclear medicine image data for determining an increase rate of blood flow under stress relative to at rest, comprising:
   storing at least part of a first myocardial nuclear medicine image data collected earlier comprising one of: myocardial nuclear medicine image data collected at rest or myocardial nuclear medicine image data collected under stress;

storing at least part of a third myocardial nuclear medicine image data collected later
comprising the other of: the myocardial nuclear medicine image data collected at rest or the myocardial nuclear medicine image data collected under stress;
storing at least part of a second myocardial nuclear medicine image data collected after a finishing collection of the first myocardial nuclear medicine image data and before starting collection of the third myocardial nuclear medicine image data, without administration of a radiopharmaceutical agent;
correcting at least part of the third myocardial nuclear medicine image data using at least part of the second myocardial nuclear medicine image data to eliminate an effect of the first myocardial nuclear medicine image data remaining in the third myocardial nuclear medicine image data; and
determining the blood flow increase rate using at least part of the first myocardial nuclear medicine image data and at least part of the third myocardial nuclear medicine image data after the correction.

2. The method according to claim 1, further comprising:
storing a heart parameter serving as a value relating to a size of a heart and storing an administered radiation dose;
converting pixel values of at least part of pixels of the image data using the stored heart parameters into standardized uptake values (SUV) in accordance with the following equation, and storing the SUVs:

SUV=Tissue radioactivity concentration/(Administered radiation dose/Value based on heart parameter); and determining the blood flow increase rate using at least part of the SUVs.

3. The method according to claim 2, wherein the heart parameter is a myocardial weight, and the value based on the heart parameter is also a myocardial weight.

4. The method according to claim 2, wherein the heart parameter is a myocardial volume, and the value based on the heart parameter is a myocardial weight calculated by multiplying the myocardial volume by a conversion factor.

5. The method according to claim 2, wherein the tissue radioactivity concentration is a value obtained by multiplying the pixel value by a becquerel calibration factor (BCF).

6. The method according to claim 5, wherein the becquerel calibration factor is subjected to collection time correction.

7. The method according to claim 1, further comprising:
converting the first to third myocardial nuclear medicine image data into two-dimensional array data or polar maps, and
calculating the myocardial blood flow increase rate using the image data after the conversion.

8. A non-transitory program storage device readable by a machine, tangibly embodying a program of instructions executable by the machine for performing operations, the operations comprising:
storing at least part of a first myocardial nuclear medicine image data collected earlier
comprising one of: myocardial nuclear medicine image data collected at rest or myocardial nuclear medicine image data collected under stress;
storing at least part of a third myocardial nuclear medicine image data collected later
comprising the other of: the myocardial nuclear medicine image data collected at rest or the myocardial nuclear medicine image data collected under stress;
storing at least part of a second myocardial nuclear medicine image data collected after finishing collection of the first myocardial nuclear medicine image data and before starting collection of the third myocardial nuclear medicine image data, without administration of a radiopharmaceutical agent;
correcting at least part of the third myocardial nuclear medicine image data using at least part of the second myocardial nuclear medicine image data to eliminate an effect of the first myocardial nuclear medicine image data remaining in the third myocardial nuclear medicine image data; and
determining blood flow increase rate using at least part of the first myocardial nuclear medicine image data and at least part of the third myocardial nuclear medicine image data after the correction.

9. The non-transitory program storage device as claimed in claim 8 where the operations further comprise:
storing a heart parameter serving as a value relating to a size of a heart and storing an administered radiation dose;
converting pixel values of at least part of pixels of the image data using the stored heart parameters into standardized uptake values (SUV) in accordance with the following equation, and storing the SUVs:

SUV=Tissue radioactivity concentration/(Administered radiation dose/Value based on heart parameter); and determining the blood flow increase rate using at least part of the SUVs.

10. The non-transitory program storage device as claimed in claim 9 where the heart parameter is a myocardial weight, and the value based on the heart parameter is also a myocardial weight.

11. The non-transitory program storage device as claimed in claim 9 where the heart parameter is a myocardial volume, and the value based on the heart parameter is a myocardial weight calculated by multiplying the myocardial volume by a conversion factor.

12. The non-transitory program storage device as claimed in claim 9 where the tissue radioactivity concentration is a value obtained by multiplying the pixel value by a becquerel calibration factor (BCF).

13. The non-transitory program storage device as claimed in claim 12 where the becquerel calibration factor is subjected to collection time correction.

14. The non-transitory program storage device as claimed in claim 9 where the operations further comprise:
converting the first to third myocardial nuclear medicine image data into two-dimensional array data or polar maps, and
calculating the myocardial blood flow increase rate using the image data after the conversion.

15. An apparatus comprising:
at least one processor; and
at least one non-transitory memory including computer program code, the at least one memory and the computer program code configured to, with the at least one processor, cause the apparatus to:
store at least part of a first myocardial nuclear medicine image data collected earlier comprising one of: myocardial nuclear medicine image data collected at rest or myocardial nuclear medicine image data collected under stress;

store at least part of a third myocardial nuclear medicine image data collected later comprising the other of: the myocardial nuclear medicine image data collected at rest or the myocardial nuclear medicine image data collected under stress;

store at least part of a second myocardial nuclear medicine image data collected after a finishing collection of the first myocardial nuclear medicine image data and before starting collection of the third myocardial nuclear medicine image data, without administration of a radiopharmaceutical agent;

correct at least part of the third myocardial nuclear medicine image data using at least part of the second myocardial nuclear medicine image data to eliminate an effect of the first myocardial nuclear medicine image data remaining in the third myocardial nuclear medicine image data; and determine blood flow increase rate using at least part of the first myocardial nuclear medicine image data and at least part of the third myocardial nuclear medicine image data after the correction.

16. The apparatus of claim 15 where the at least one memory and the computer program code are configured to, with the at least one processor, cause the apparatus to:

store a heart parameter serving as a value relating to a size of a heart and store an administered radiation dose;

convert pixel values of at least part of pixels of the image data using the stored heart parameters into standardized uptake values (SUV) in accordance with the following equation, and storing the SUVs:

SUV=Tissue radioactivity concentration/(Administered radiation dose/Value based on heart parameter); and determine the blood flow increase rate using at least part of the SUVs.

17. The apparatus of claim 16 where the heart parameter is a myocardial weight, and the value based on the heart parameter is also a myocardial weight.

18. The apparatus of in claim 16 where the heart parameter is a myocardial volume, and the value based on the heart parameter is a myocardial weight calculated by multiplying the myocardial volume by a conversion factor.

19. The apparatus of claim 16 where the tissue radioactivity concentration is a value obtained by multiplying the pixel value by a becquerel calibration factor (BCF).

20. The apparatus of claim 19 where the becquerel calibration factor is subjected to collection time correction.

21. The apparatus of claim 15 where the at least one memory and the computer program code are configured to, with the at least one processor, cause the apparatus to:

convert the first to third myocardial nuclear medicine image data into two-dimensional array data or polar maps, and calculate the myocardial blood flow increase rate using the image data after the conversion.

* * * * *